United States Patent
Umapathy et al.

(10) Patent No.: US 9,983,136 B2
(45) Date of Patent: *May 29, 2018

(54) METHOD AND AN APPARATUS FOR OBTAINING SAMPLE SPECIFIC SIGNATURES

(71) Applicant: INDIAN INSTITUTE OF SCIENCE, Karnataka (IN)

(72) Inventors: Siva Umapathy, Bangalore (IN); Sanchita Sil, West Bengalore (IN); John Kiran, Hassan (IN)

(73) Assignee: INDIAN INSTITUTE OF SCIENCE, Bangalore (IN)

( * ) Notice: Subject to any disclaimer, the term of this patent is extended or adjusted under 35 U.S.C. 154(b) by 0 days. days.

This patent is subject to a terminal disclaimer.

(21) Appl. No.: 14/374,933

(22) PCT Filed: Sep. 2, 2013

(86) PCT No.: PCT/IN2013/000538
§ 371 (c)(1),
(2) Date: Jul. 28, 2014

(87) PCT Pub. No.: WO2014/192007
PCT Pub. Date: Dec. 4, 2014

(65) Prior Publication Data
US 2016/0103069 A1    Apr. 14, 2016

(30) Foreign Application Priority Data
May 27, 2013 (IN) .......................... 2312/CHE/2013

(51) Int. Cl.
*G01N 21/65* (2006.01)
*G01J 3/44* (2006.01)

(52) U.S. Cl.
CPC ............ *G01N 21/65* (2013.01); *G01J 3/4412* (2013.01); *G01N 2201/068* (2013.01); *G01N 2201/06113* (2013.01); *G01N 2201/129* (2013.01)

(58) Field of Classification Search
CPC . G01B 21/65; G01J 3/4412; G01N 2201/068; G01N 2201/06113; G01N 2201/129
See application file for complete search history.

(56) References Cited

U.S. PATENT DOCUMENTS

| | | | |
|---|---|---|---|
| 8,269,174 B2 | 9/2012 | Gardner et al. | |
| 2002/0133065 A1 | 9/2002 | Lucassen et al. | |
| 2003/0059778 A1* | 3/2003 | Berlin ................. | C12Q 1/6869 435/6.13 |
| 2008/0268548 A1* | 10/2008 | Zuckerman .......... | G01N 21/658 436/172 |
| 2009/0141271 A1 | 6/2009 | Matousek et al. | |

(Continued)

*Primary Examiner* — Dominic J Bologna
(74) *Attorney, Agent, or Firm* — Mark M. Friedman (57) ABSTRACT

The invention provides a method for obtaining sample specific signatures. The method comprises of irradiating the sample at a predefined location with an electromagnetic radiation of specific wavelength; selectively capturing a certain component of the scattered electromagnetic radiation to obtain a plurality of profiles; and filtering the profiles to obtain a sample specific signature. The invention provides an apparatus for obtaining sample specific signatures.

14 Claims, 9 Drawing Sheets

(56) References Cited

U.S. PATENT DOCUMENTS

| | | | | |
|---|---|---|---|---|
| 2010/0038550 A1* | 2/2010 | DeVito | ............... | G01V 5/0069 250/370.11 |
| 2010/0110425 A1* | 5/2010 | Matousek | ................. | G01J 3/10 356/301 |
| 2010/0148073 A1* | 6/2010 | Nelson | .................. | G01J 3/2803 250/362 |
| 2013/0135609 A1* | 5/2013 | Gardner, Jr. | ............. | G01J 3/44 356/51 |

* cited by examiner

FIG. 8

METHOD AND AN APPARATUS FOR OBTAINING SAMPLE SPECIFIC SIGNATURES

FIELD OF INVENTION

The invention generally relates to the field of physical chemistry and particularly to a method and an apparatus for obtaining sample specific signatures, using Raman spectroscopy.

BACKGROUND

Spectroscopic techniques including but not limited to dynamic light scattering, photon correlation spectroscopy and fluorescence correlation spectroscopy have been adopted for studying strongly scattering media such as colloids, gels and tissues. The techniques mentioned above are derived from Rayleigh scattering and/or fluorescence phenomenon. One of the advantages of multiple Rayleigh scattering in strongly scattering media has been the study of dynamics of particles in motion in any given sample. Also the multiple Rayleigh scattering enables estimation of the size distribution of particles in the sample. Another application of Rayleigh scattering has been in areas including but not limited to non-invasive depth profiling and neuro-imaging. However, the scattering profile does not identify the type of materials present in the sample.

Since the multiply scattered light contains both Rayleigh and Raman scattered photons, recording Raman scattered light has been explored for identifying the structure and chemical nature of the molecules. Examples of known techniques that record Raman scattering include but are not limited to Spatially Offset Raman Spectroscopy (SORS), Surface Enhanced Raman Spectroscopy (SERS) and transmission Raman spectroscopy (TRS). SORS works on the principle of backscattering collection geometry wherein the scatterers close to the surface contribute more to the Raman signal than the scatterers located deeper in the sample. SERS works on the principle of Raman light amplification in the presence of a noble metal surface that results in chemical and surface plasmon resonance enhancements of the incident electromagnetic field. One of the primary disadvantages of SORS, SERS and TRS is that the detection is restricted to a specific experimental geometry. For example, SORS works only in the backscattering geometry; SERS relies on metal surface for amplification and TRS cannot distinguish the individual layers of different chemicals in a multi-component layered system. Further, the depth at which detection is effective is limited up to few mm, for example 3 mm. Hence, there is a need for method that can profile samples at various levels of depth.

BRIEF DESCRIPTION OF DRAWINGS

So that the manner in which the recited features of the invention can be understood in detail, some of the embodiments are illustrated in the appended drawings. It is to be noted, however, that the appended drawings illustrate only typical embodiments of this invention and are therefore not to be considered limiting of its scope, for the invention may admit to other equally effective embodiments.

SUMMARY OF THE INVENTION

One aspect of the invention provides a method for obtaining sample specific signatures. The method comprises of irradiating the sample at a predefined location with an electromagnetic radiation of specific wavelength; selectively capturing a certain component of the scattered electromagnetic radiation to obtain a plurality of profiles; and filtering the profiles to obtain a sample specific signature.

Another aspect of the invention provides an apparatus for obtaining sample specific signatures.

DETAIL DESCRIPTION OF THE INVENTION

Various embodiments of the invention provide a method and an apparatus for obtaining sample specific signatures. The method works on the principle of amplification of Raman signal through multiple scattering of light in a randomly distributed medium. The multiply amplified Raman signal enables the method to probe both strongly and weakly scattering media. The multiple scattering can be seen as an amplifying process of Raman light by the medium due to the presence of incident and Rayleigh scattered light. An optical signal corresponding to a particular Raman shift from a molecule can be amplified by subsequent addition of similar Raman photons generated by other similar molecules through multiple scattering due to the presence of incident and Rayleigh scattered photons.

Each particle in a sample is excited by the external electromagnetic field and the resultant field scattered by all other particles. In one embodiment of the invention, the irradiation can be achieved by at least one source of electromagnetic radiation placed at a distance from the sample. The field scattered by the particle depends on the total field to which it is exposed. The light scattered at other positions in the medium contribute to the irradiance at a position of observation. Therefore, the scattered light merely changes direction and is lost from a beam propagating in a particular direction, but contributes to other directions. When there are many particles and their separation is random, the scattered field will be incoherent, i.e., there is no systematic relation among the phases of the waves scattered by the individual particles. Thus, the total irradiance scattered by the collection in any direction is the sum of the irradiances scattered by the individual particles in that direction. The total signal observed at any point of observation is dependent on the scattering cross section, the number density of particles and the medium thickness. Therefore, amplified Raman signal can enable us to probe dense media of thickness exceeding a few tens of millimeter and probe samples buried deep inside them. Since Raman signals obtained are specific to the scatter of the source, accurate profiling of substances, to obtain specific chemical signatures, is possible irrespective of the extent to which the source is scattered. The signatures obtained includes but is not limited to spectral graphs, images and all such depictions capable of determining the chemical structure.

Figure 1A:
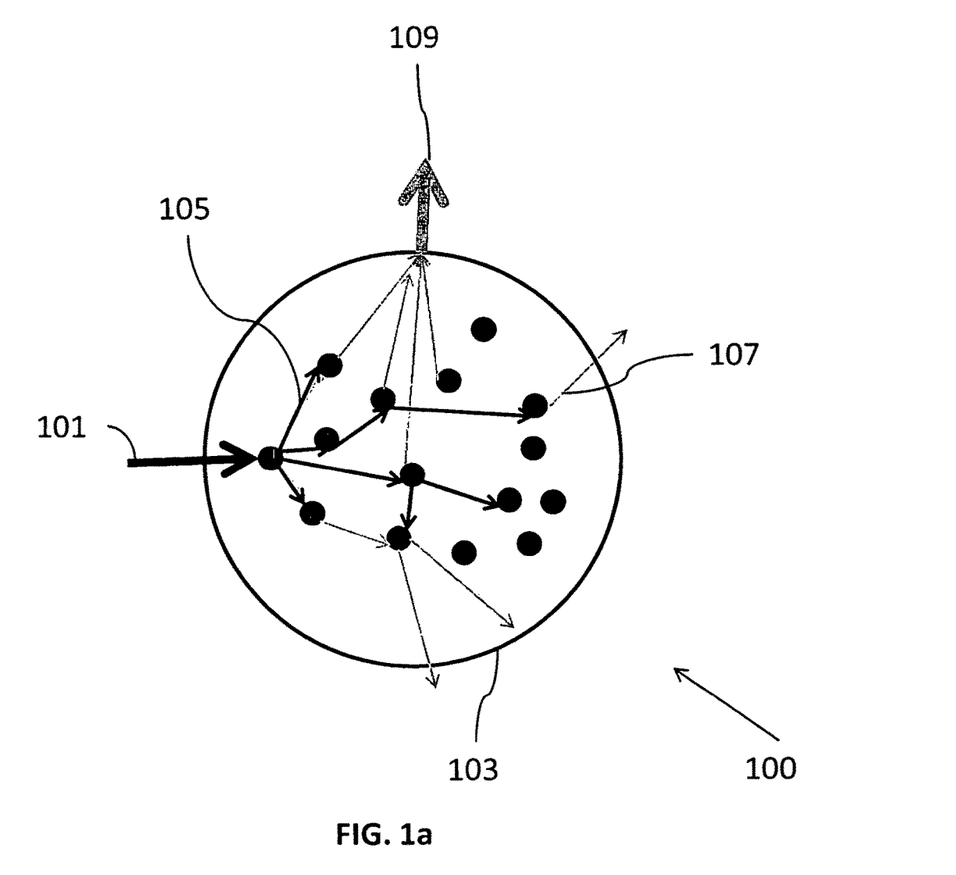
FIG. 1 illustrates the principle of multiple Raman scattering in non homogeneous or homogeneous medium, according to an embodiment of the invention.

FIG. 1 illustrates the principle of multiple Raman scattering in a non homogenous medium, according to an embodiment of the invention. A monochromatic coherent source of light 101 is incident either in single location or at multiple points on a non homogenous sample 103. The incident light 101 is scattered by the sample 103. The scattered light includes both elastic (Rayleigh) 105 and inelastic (Raman) scattering 107. The inelastic or the Raman scattered light can emerge out of the sample at multiple directions due to multiple continuous scattering. The diagram shows one such situation where Raman photons add up in certain directions due to sequential scattering events, resulting in a detectable signal 109.

Figure 2A:
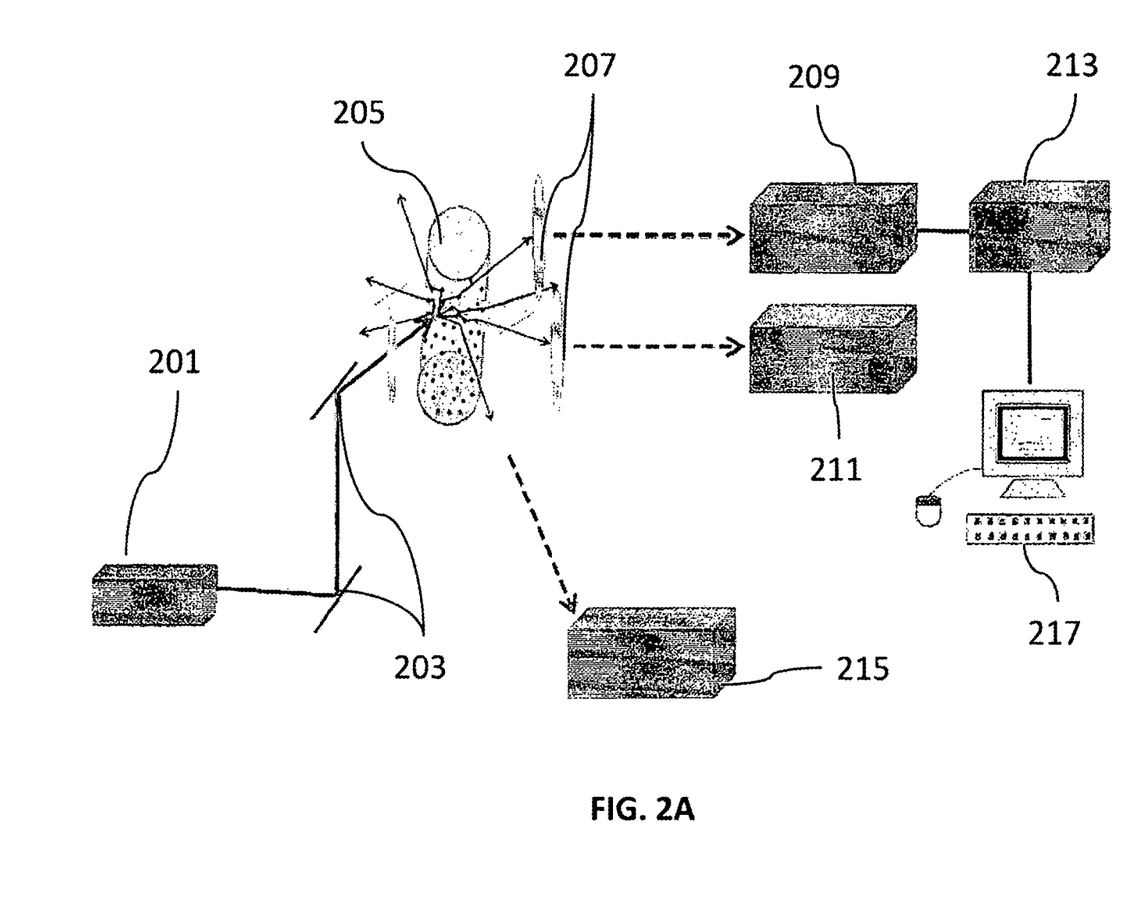
FIG. 2a shows a block diagram of an apparatus for obtaining sample specific signatures, according to an embodiment of the invention.

FIG. 2a shows a block diagram of an apparatus for detection of molecular structure of chemical compounds in multilayered sample, according to an embodiment of the invention. The apparatus includes a source of electromagnetic radiation 201. A lens arrangement 203 focuses the source 201 onto a non homogenous or homogeneous sample 205. A plurality of collection lenses 207 are placed at various locations around the sample 205. The collection lenses 207 focuses the scattered Raman photons onto a spectrometer 209. A detector 213 is coupled to the spectrometer 209. The output of the detector 213 is sent to an analysis unit 217 for estimating various parameters.

In one embodiment of the invention, the electromagnetic radiation is a monochromatic coherent source of light. In an example of the invention a single source of electromagnetic radiation is used for irradiation. Alternatively multiple sources of electromagnetic radiation can be used for irradiating the sample at a plurality of positions. Different wavelength excitation source in the range of 500 nm to 1400 nm can be used for these experiments. The spectral range is dependent on the spectrometer and the detector and the penetration depth depends upon on the selection of the source wavelength. In one example of the invention, the wavelength of the source of light for excitation is chosen in the near IR region. The 830 nm laser is preferred over visible light for investigating strongly scattering media in order to avoid fluorescence and absorption, and to attain a better penetration depth. The laser beam is focused onto the sample using an optical directing element. The optical directing element is selected from a group including but not limited to lens, mirrors and a combination thereof. In an example of the invention a plano-convex lens is used as an optical directing element. In an alternate embodiment of the invention, the sample can be irradiated directly from the electromagnetic source. The incident beam polarization is perpendicular to the plane of observation of the scattered light. The Raman signals are collected from the samples using a 50-mm diameter biconvex lens (f/4.14) and imaged onto the spectrometer slit with a magnification of 2. The f- number matching between the collection lens and the spectrometer is achieved through appropriate optics. The spectrometer entrance slit is adjusted to obtain the best spectral resolution possible. Laser line filters such as notch filters, are used in front of the entrance slit to eliminate the Rayleigh scattered light.

The samples taken for study includes but is not limited to solid powders filled in custom made glass cuvettes, liquids/solids filled in commercial high density polyethylene (HDPE) containers and pharmaceutical tablets. A bilayer cuvette is obtained by gluing two quartz plates. Alternatively BK7 glass plates can be used for constructing the bilayer.

Figure 2B:
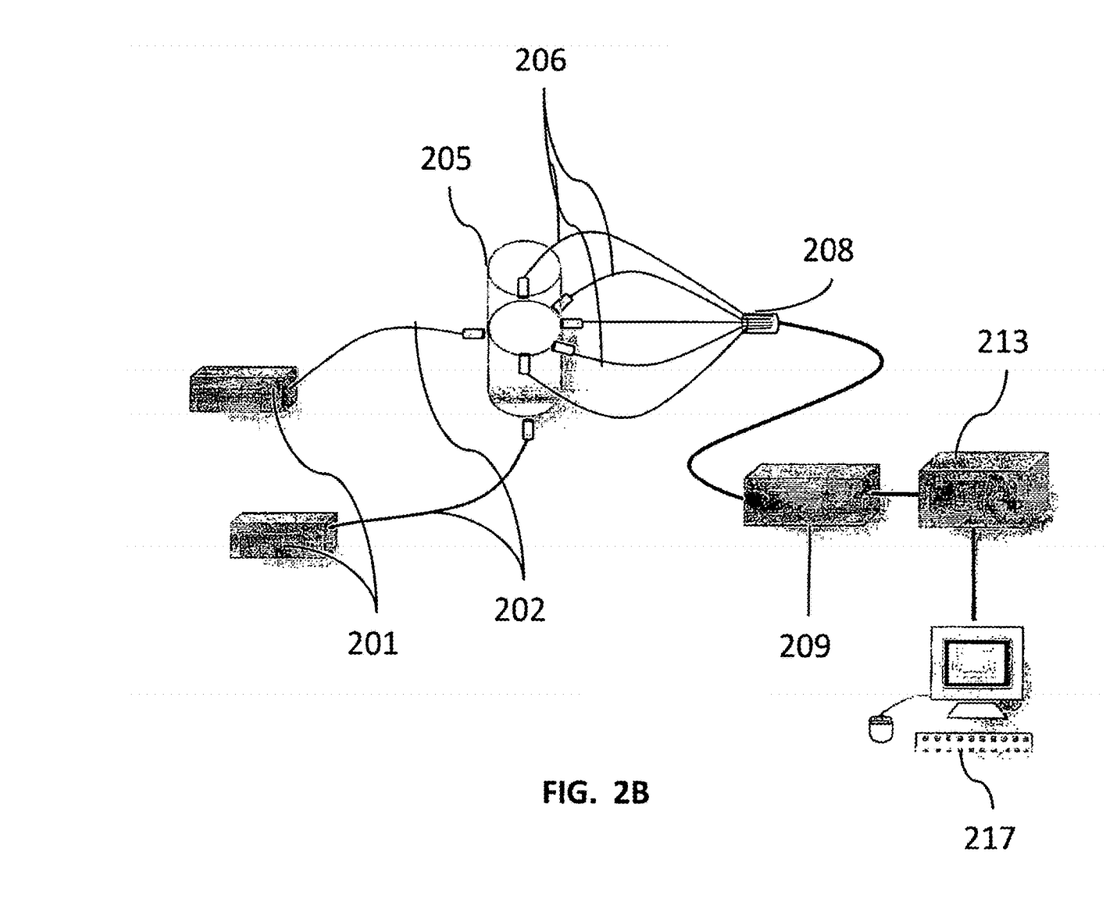
FIG. 2b shows an arrangement for multipoint detection of sample specific signatures, according to an alternate embodiment of the invention.

FIG. 2b shows an arrangement for multipoint detection of molecular structure of chemical compounds in multilayered sample, according to an alternate embodiment of the invention. The laser beam from a source 201 is delivered through an optical fiber 202 to the sample 205. The Raman signals are collected using a plurality of fibers 206 attached to the sample container 205 at varying angles with respect to the incident beam. The fibers 206 are bundled and placed in front of collection optics arrangement 208 fixed to the entrance slit of the spectrometer 209.

The apparatus as described herein is used for detecting specific chemical signatures of the scattering samples. The chemical signatures can be identified independent of the collection angle. The Raman signals are collected from all sides of sample. The experimental apparatus as described herein enables the collection of Raman signals from the samples in any collection geometry. The collection geometry as referred herein means orientation and position of the collection arrangement. The collection arrangement includes but is not limited to lenses, fiber optics and all such devices capable of capturing the scattered electromagnetic radiation, as obvious to a person skilled in the art, from the sample. The same apparatus can be used for Raman imaging experiments.

Figure 3:
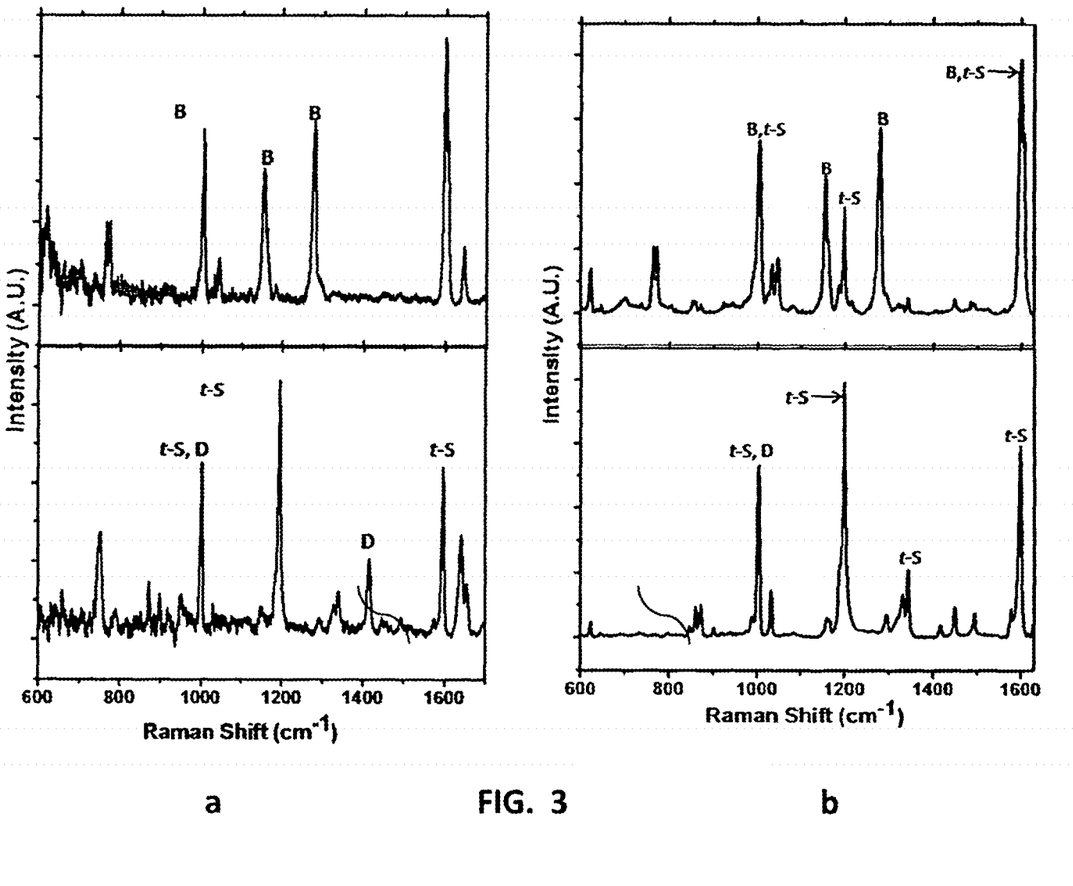
FIG. 3 shows specific detection of t-stilbene in a solid-solid bilayer sample comprising a) 4-BBP and b) DFBP, according to an embodiment of the invention.

FIG. 3 shows specific detection of t-stilbene in a in a solid-solid bilayer sample comprising a) 4-BBP and b) DFBP, according to an embodiment of the invention. The powder samples are taken in multilayer glass cuvettes. In one example, the solid-solid bilayer included a top layer comprising of a 2 mm thick layer of decafluorobenzophenone (DFBP) and a bottom layer comprising of 1 mm thick layer of trans-stilbene. In another example the solid-solid bilayer included a top layer comprising of a 2 mm thick layer of 4-benzoylbiphenyl (4BBP) and a bottom layer comprising of a 1 mm thick layer of trans-stilbene. The laser beam is focused onto the top layer and the signal is collected in different geometries possible. The grain size of 4BBP powder was much smaller than that of DFBP. The Raman signal from the bottom layer showed sensitivity to the particle size and density of the top layer in different experimental geometries. The trans-stilbene could be detected through the DFBP layer when the signal was collected from the illuminated sample area under backscattering geometry. However, no signal could be detected from it through 4BBP top layer when the signal was collected from the illuminated sample area under backscattering geometry.

Figure 4:
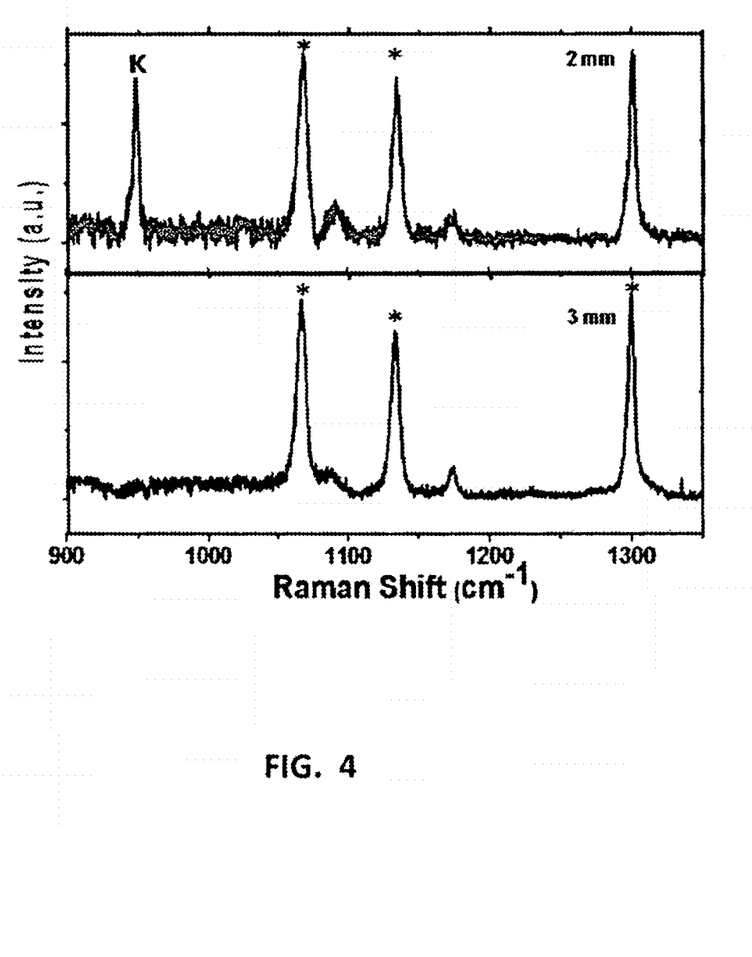
FIG. 4 shows specific detection of $KClO_4$ in HDPE containers of different wall thicknesses through back scattering mode, according to an embodiment of the invention.
Figure 5:
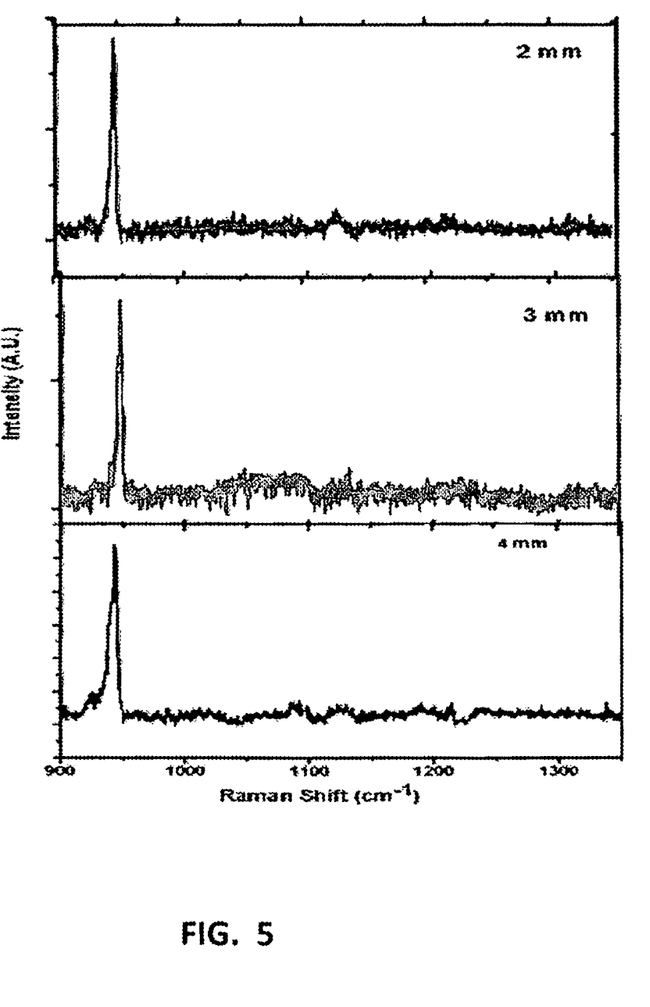
FIG. 5 shows specific detection of $KClO_4$ in HDPE containers of different wall thicknesses through transmission mode, according to an embodiment of the invention.
Figure 6:
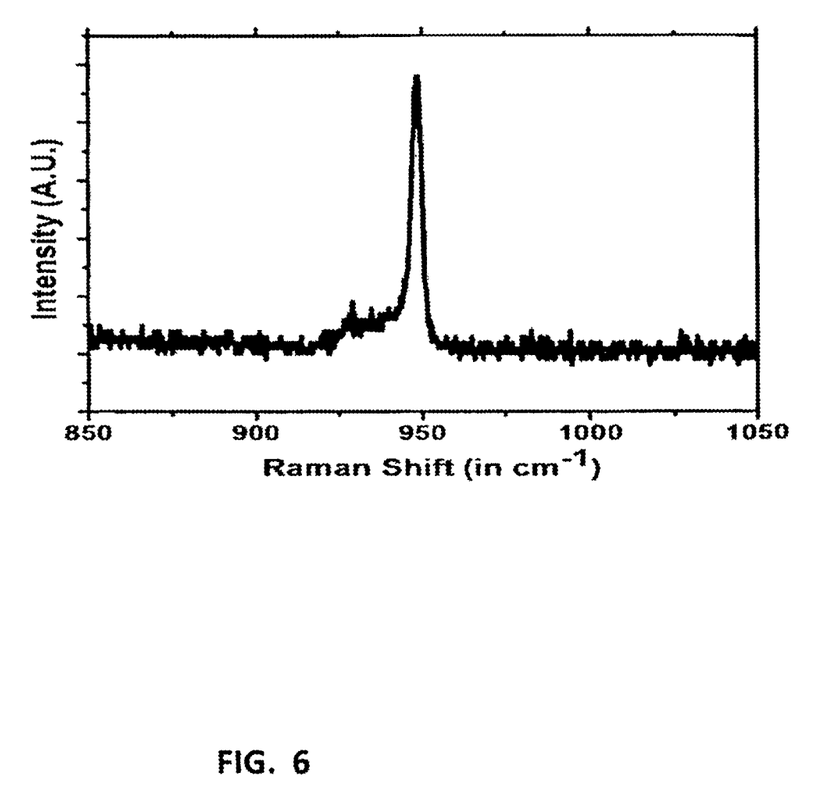
FIG. 6 shows specific detection of $KClO_4$ in a HDPE container of wall thicknesses of 3 mm using optical fibers arranged in one plane on all sides of the container, according to an embodiment of the invention.

FIG. 4 shows specific detection of $KClO_4$ in HDPE containers of different wall thicknesses through back scattering mode, according to an embodiment of the invention. As the thickness of the container is increased from 2 mm to 3 mm, the Raman signal from $KClO_4$ is not observed in the back scattering mode. The sensitivity of the Raman signal to the particle size and density of the top layer is utilized in detection of powdered sample of $KClO_4$ filled in HDPE containers of varying wall thickness. FIG. 5 shows specific detection of $KClO_4$ in HDPE containers of different wall thicknesses through transmission mode, according to an embodiment of the invention. FIG. 6 shows specific detection of $KClO_4$ in a HDPE container of wall thicknesses of 3 mm using optical fibers arranged in one plane on all sides of the container, according to an embodiment of the invention.

Figure 7:
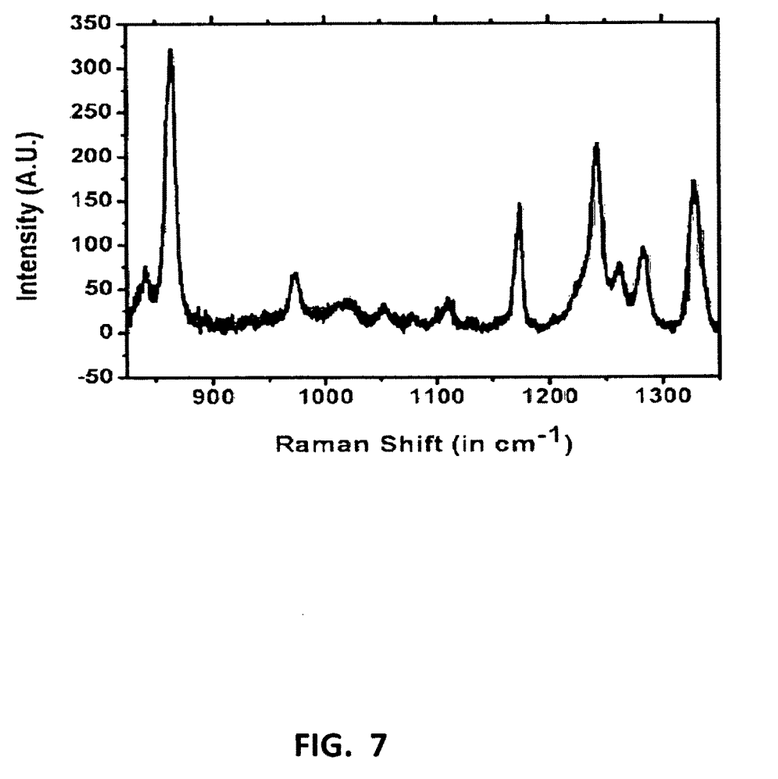
FIG. 7 shows analysis of a 7-mm thick Hostaflam tablet using transmission geometry, according to an embodiment of the invention.

FIG. 7 shows analysis of a 7-mm thick Hostaflam tablet using transmission geometry, according to an embodiment of the invention. It can be noticed that except for the backscattering geometry, the container signal is suppressed appreciably in other geometries. This is possible in geometries such as sideways and transmission because of long migration time available to amplification of Raman photons in a non-absorbing powder media.

Figure 8:
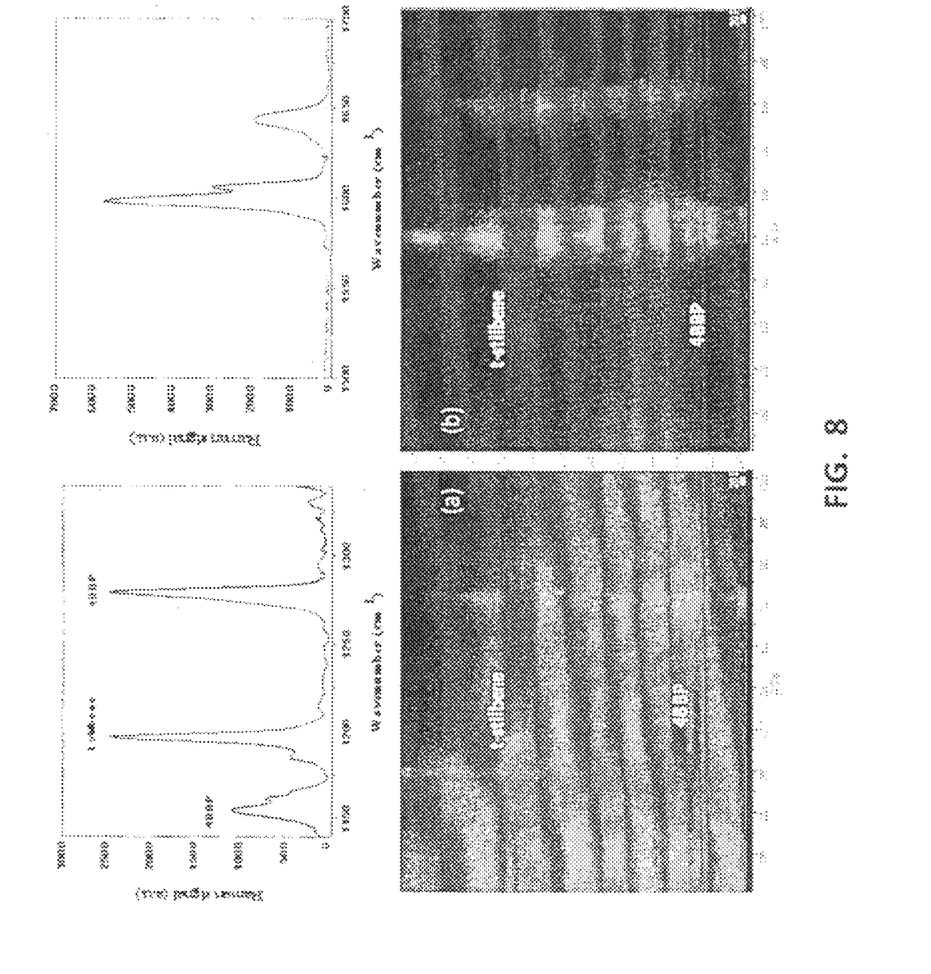
FIG. 8 shows backscattering Raman images from a stacked solid-solid bilayer, according to an embodiment of the invention.

FIG. 8 shows backscattering Raman images from a stacked solid-solid bilayer, according to an embodiment of the invention. The Raman imaging experiment is done on stacked powder layers. The experiment can be performed in varied geometries including but not limited to backscattering, all sides and transmission. FIG. 8 demonstrates the Raman images from upper and lower solid powder layers formed on a charge coupled device CCD. A circular convex lens or a cylindrical lens is used to focus laser beam to the interface of the two layers and a short focal length, large biconvex lens or a cylindrical lens is used to image the sample on to the CCD. As shown in FIG. 8, imaging can clearly separate the overlapping peaks from different samples and reveal the information about different samples. The Raman imaging can be extended to build a transmission type Raman imaging system for chemical compounds in nonmetallic, opaque containers.

The invention described herein provides a method and an apparatus for obtaining sample specific signatures. The method predominantly utilizes a Raman spectroscopic technique that is geometry independent. The spectroscopic technique is capable of probing any type of scattering samples and identifies individual layers in a multilayer system. The primary advantages of the method and the apparatus described herein is that the method is independent of the experimental geometry. Further, the apparatus is configured to perform at any point of need location. Examples of point of need location include but is not limited to airports, railway stations, bus stations, restaurants, cargo collection centers all such public places where such sample specific signatures are needed. Also, the method as described herein is capable of obtaining sample specific signatures in a multilayer sample wherein the thickness of the multilayer is at least 5 mm. The non dependence on the geometry enables collection of Raman signals from samples lying within other scattering materials for example, a dense plastic container, using either conventional lenses and/or optical fibers placed at different positions around the sample. The technique basically depends on recording multiply amplified Raman signal of target materials coming out in all directions.

The other advantages of the method, as described herein above include but are not limited to:

Obtaining chemical composition of any scattering media.
Identification of the chemical composition of the substances obscured by layers.
Flexibility to use any experimental geometry for studying scattering systems.
Multi point signal collection irrespective of the point of illumination.
Signals with good spectral resolution and signal to noise ratio.
Study the dynamics of the strongly scattering media.
Determining of food quality and adulteration in food using this technique in area of food technology.
Application in pharmaceutical industry for quality control and process monitoring
Screening of contraband materials, counterfeit items packed in containers/packages in the field of forensic science.
Study of mineral ores and inclusions in mines and ore samples.
Oil spills and leakages in oil fields, sea.
Frequency specific Raman imaging of strongly scattering media such as biological tissues, much similar to the infra-red imaging for detection of cancer and other medical applications involving sub-surface information.

The invention as described herein above provides a method for obtaining sample specific signatures. The method predominantly works on the principle of detecting multiply amplified Raman scattering from the sample. The detection principle is independent of the nature of the sample, collection geometry and is capable of obtaining sample specific signatures in the multilayer sample wherein the thickness of the multilayer is at least 5 mm. The invention also provides an apparatus for obtaining sample specific signatures. The apparatus can be moved to any point of need location for obtaining the sample specific signatures.

The foregoing description of the invention has been set for merely to illustrate the invention and is not intended to be limiting. Since modifications of the disclosed embodiments incorporating the spirit and substance of the invention may occur to person skilled in the art, the invention should be construed to include everything within the scope of the appended claims and equivalents thereof.

We claim:

1. A method for obtaining sample specific signatures, the method comprising:
    irradiating a sample at a predefined location with an electromagnetic radiation of a specific wavelength to cause electromagnetic radiation to be scattered from the sample;
    selectively capturing, a certain component of scattered electromagnetic radiation from at least one of a-various locations around the sample to obtain from a cross section of said radiation a plurality of profiles; and
    filtering the profiles to obtain a sample specific signature;
    wherein said various locations around the sample include an incident direction of said electromagnetic radiation of a specific wavelength;
    wherein each particle in the sample is excited by both said electromagnetic radiation and a resultant field scattered by all other particles in the sample; and
    wherein a signal observed at any point of observation is dependent on a cross section of the resultant field and a number density of particles.

2. The method according to claim 1, wherein the predefined location is at least one position around the sample.

3. The method according to claim 1, whet the wavelength of the electromagnetic radiation is in the range of 500 nm to 1400 nm.

4. The method according to claim 1, wherein the component of the scattered electromagnetic radiation is a multiply amplified Raman scattering.

5. The method according to claim 1, wherein the selective capturing of the scattered electromagnetic radiation is independent of collection angle.

6. The method according to claim 1, wherein the captured electromagnetic radiation is from an amplified scattering obtained through multiple scattering of the incident electromagnetic radiation.

7. The method according to claim 1, wherein the sample specific signatures are from a multilayer sample wherein the thickness of the multilayer is at least 5 mm.

8. An apparatus for detection of sample specific signatures, the apparatus comprising:
   at least one electromagnetic radiation source;
   a first arrangement for directing electromagnetic radiation onto a sample such that said electromagnetic radiation is scattered from the sample;
   a second, arrangement for collecting scattered electromagnetic radiation from the sample;
   a spectrum analyzer operably coupled to the second arrangement; and
   a detector connected to the optical spectrum analyser and being configured to selectively capture a certain component of said scattered electromagnetic radiation from at least one of various locations around the sample to obtain from a cross section of said radiation a plurality of profiles;
wherein said various locations around the sample include an incident direction of said electromagnetic radiation of a specific wavelength;
wherein each particle in the sample is excited by both said electromagnetic radiation and a resultant field scattered by all other particles in the sample; and
wherein a signal observed at any point of observation is dependent on a cross section of the resultant field and a number density of particles.

9. The apparatus according to claim 8, wherein the first arrangement comprises:
   at least one optical fiber wherein each of the at least one optical fiber is connected to each of the at least one electromagnetic radiation, source; and
   at least one directing optical element comprising a lens, a mirror or a combination thereof wherein the directing element is positioned to direct, the electromagnetic radiation onto the sample.

10. The apparatus according to claim 8, wherein the second arrangement is a plurality of optical elements positioned to direct the scattered electromagnetic radiation to the spectrum analyzer.

11. The apparatus according to claim 8, wherein the positioning of the second arrangement is independent of the orientation and/or position of the arrangement at the sample.

12. The apparatus according to claim 8, wherein the second arrangement is a plurality of optical fibers positioned at various locations on the sample for collecting the scattered electromagnetic radiation.

13. The apparatus according to claim 8, wherein the analyser comprises:
   a spectrometer;
   a filter for selectively capturing the scattered electromagnetic radiation; and
   an analysis unit for obtaining a sample specific profile.

14. The apparatus according to claim 8, wherein the apparatus is configured for providing sample specific signatures at any point-of-need location.

* * * * *

UNITED STATES PATENT AND TRADEMARK OFFICE
CERTIFICATE OF CORRECTION

| | |
|---|---|
| PATENT NO. | : 9,983,136 B2 |
| APPLICATION NO. | : 14/374933 |
| DATED | : May 29, 2018 |
| INVENTOR(S) | : Siva Umapathy |

It is certified that error appears in the above-identified patent and that said Letters Patent is hereby corrected as shown below:

In the Claims

Claim 1, Column 6, Line 44:
Change "ELECTROMAGNETIC RADIATION FROM AT LEAST ONE OF A-VARIOUS"
To -- ELECTROMAGNETIC RADIATION FROM AT LEAST ONE OF VARIOUS --

Signed and Sealed this
Seventeenth Day of July, 2018

Andrei Iancu
*Director of the United States Patent and Trademark Office*